US008428881B2

(12) United States Patent
Winfield et al.

(10) Patent No.: US 8,428,881 B2
(45) Date of Patent: Apr. 23, 2013

(54) SYSTEM AND METHODS FOR NON-TARGETED PROCESSING OF CHROMATOGRAPHIC DATA

(75) Inventors: Stephanie Winfield, Raleigh, NC (US); William David Haas, Durham, NC (US); Marie Coffin, Cary, NC (US)

(73) Assignee: Metabolon, Inc., Durham, NC (US)

( * ) Notice: Subject to any disclaimer, the term of this patent is extended or adjusted under 35 U.S.C. 154(b) by 1767 days.

(21) Appl. No.: 11/016,612

(22) Filed: Dec. 17, 2004

(65) Prior Publication Data

US 2005/0143931 A1 Jun. 30, 2005

Related U.S. Application Data

(60) Provisional application No. 60/531,226, filed on Dec. 19, 2003.

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC .................. 702/19; 702/20; 703/11; 703/12

(58) Field of Classification Search ........................ None
See application file for complete search history.

(56) References Cited

U.S. PATENT DOCUMENTS

| | | | |
|---|---|---|---|
| 4,422,459 A | 12/1983 | Simson | |
| 5,263,120 A * | 11/1993 | Bickel | 706/62 |
| 5,672,869 A | 9/1997 | Windig et al. | |
| 6,873,915 B2 * | 3/2005 | Hastings | 702/22 |
| 2001/0037178 A1 * | 11/2001 | Bush | 702/14 |
| 2004/0181345 A1 * | 9/2004 | Kolossov et al. | 702/22 |

OTHER PUBLICATIONS

Vassiliadis, S.; Triantafyllos, G.; Pechanek, G.G., "A method for computing the most typical fuzzy expected value," Fuzzy Systems, 1994. IEEE World Congress on Computational Intelligence., Proceedings of the Third IEEE Conference on , vol. No. pp. 2040-2045 vol. 3, Jun. 26-29, 1994.*
TargetDB, "Target Database for Structural Biology," (Downloaded from the Internet on Oct. 14, 2011).
Nicholson et al., "Metabonomics: A Platform for Studying Drug Toxicity and Gene Function," Nature Reviews Drug Discovery, vol. 1, pp. 153-161 (Feb. 2002).
Watkins et al., "Toward the Implementation of Metabolomic Assessments of Human Health and Nutrition," Current Opinion in Biotechnology, vol. 13, Issue 5, pp. 512-516 (Oct. 2002).

(Continued)

*Primary Examiner* — Larry D Riggs, II
(74) *Attorney, Agent, or Firm* — Jenkins, Wilson, Taylor & Hunt, P.A.

(57) ABSTRACT

Methods for processing hyphenated chromatographic data to delineate components of a sample are disclosed. According to one aspect, the method includes obtaining hyphenated chromatographic data points for a sample, each data point comprising at least three dimensions, one of the dimensions being a continuous dimension, and subjecting at least a portion of the data points to an algorithm that organizes the data points into discrete clusters according to the data points' continuous dimension values by starting at either a smallest or largest value and delineating at a largest gap between adjacent values within a predetermined resolution window, wherein the resulting clusters are of varying width of less than or equal to the width of the resolution window and wherein at least some of the clusters are indicative of components of the sample.

33 Claims, 4 Drawing Sheets

OTHER PUBLICATIONS

"Data Explorer Software; Version 4 Series Software; User Guide," Applied Biosystems, pp. 1-447 (Copyright 2001).

Abbassi et al., "Automatic Extraction of Relevant Peaks and Reconstruction of Mass Spectra for Low Signal-to-Noise GC-MS Data," International Journal of Mass Spectrometry and Ion Processes, vol. 141, pp. 171-186 (1995).

Barry, "The Effect of Detector Gas Purity on FID Baseline Stability," Goodley & Imitani, American Laboratory, pp. 36B-36D (Apr. 1993).

Hamilton et al., "Mixture Analysis Using Factor Analysis. II: Self-Modeling Curve Resolution," Journal of Chemometrics, vol. 4, Issue 1, pp. 1-13 (Jan. 1990).

Dromery et al., "Extraction of Mass Spectra Free of Background and Neighboring Component Contributions From Gas Chromatography/Mass Spectrometry Data," Analytical Chemistry, vol. 48, No. 9, pp. 1368-1375 (Aug. 1976).

Biller et al., "Reconstructed Mass Spectra, A Novel Approach for the Utilization of Gas Chromatograph—Mass Spectrometer Data," Analytical Letters, vol. 7, No. 7, pp. 515-528 (1974).

* cited by examiner

SYSTEM AND METHODS FOR NON-TARGETED PROCESSING OF CHROMATOGRAPHIC DATA

RELATED APPLICATIONS

This application claims the benefit of U.S. provisional application Ser. No. 60/531,226, filed 19 Dec. 2003, the contents of which is herein incorporated by reference in its entirety.

FIELD OF THE INVENTION

The invention relates generally to systems and methods for processing hyphenated chromatographic data. The methods of the invention are particularly useful for the non-targeted processing of data collected from biological samples by a combination of chromatographic and spectroscopic techniques such as gas or liquid chromatography followed by mass spectrometry.

BACKGROUND OF THE INVENTION

Metabolic profiling or metabolomics is emerging as an important new methodology focused on the quantitative analysis of low molecular weight endogenous biochemicals in cells, biofluids, or tissues. Nicholson et al., 1 Nat. Rev. Drug Discov. 153-61 (2002); Watkins & German, 3 Curr. Opin. Biotechnol. 512-6 (2002). In contrast to traditional approaches where a particular compound, or group of compounds, is targeted in a sample, metabolic profiling (or biochemical profiling) is a comprehensive measurement of the biochemical makeup of a sample. Metabolic profiling is often referred to as a "global" or "non-targeted" approach. Biological samples are generally complex mixtures of unknown compounds and, therefore, metabolic profiling generally involves collection of a large amount of data and subsequent mining of the data for new correlations and patterns.

Metabolic profiling is generally performed using a chromatography step followed by a spectroscopic step, and use of such methodology results in the generation of complex chromatographic data sets. Using any one of gas or liquid chromatography-mass spectrometry (GC-MS; LC-MS), liquid chromatography-NMR (LC-NMR) and liquid chromatography-ultra violet spectroscopy (LC-UV) enable simultaneous detection and quantification of a broad range of biochemicals in biological samples. MS methods generally offer the greatest sensitivity and, thus, are generally best suited for metabolic profiling.

Due to the complexity of data collected for a broad range of compounds in a biological sample, extracting meaningful information is difficult, even with recent advances in instrument hardware and computer systems resulting in increased sensitivity and resolution. For example, high background and noise levels generally associated with electrospray LC-MS data make visual analysis difficult with respect to identification of the components present as often, few if any, distinct peaks are observable. Manual examination is frequently employed to extract a list of masses of components that appear to be "real," a method that is not only time-consuming and tedious, but also one that may result in failure to identify highly overlapping and/or minor components. Similarly, use of available processing algorithms for non-targeted extraction of information from such data generally results in a loss of information and an introduction of error.

Algorithms for extracting information from chromatographic data include the Biller Biemann algorithm for resolution enhancement to separate overlapping peaks. Biller & Biemann, 7 Anal. Letters 515-28 (1974); Dromery et al., 48 Anal. Chem. 1368-75 (1976). Although the method works well for high quality data, i.e. where the peaks can clearly be discriminated from the background signal, the algorithm does not perform well for data having a high amount of noise, such as LC-MS data. Similarly, background subtraction can be performed as described by Goodley & Imitani, 25 Am. Lab 36B-36D (1993), but is of limited use for complex data in which the background is not constant over the duration of the chromatographic analysis.

The majority of recent methods for extraction of information from chromatographic data are in the field of curve resolution, such as that described by Hamilton & Gemperline, 4 Chemometrics 1-13 (1990). While curve resolution techniques are generally able to resolve overlapping peaks in chromatographic data with low background and noise levels, the techniques have limitations when applied to chromatographic data in which chromatograms of a single dimension (e.g., mass chromatograms) contain multiple peaks. Mass chromatograms with more than one peak are not uncommon in GC- and LC-MS, due to the presence of isomers and components with common fragments. As curve resolution techniques fail to resolve multiple peaks having a single chromatographic dimension, the techniques are generally of limited value for use in analyzing metabolic profiling data. Abbassi et al. have described an automated approach for the extraction of peaks from GC-MS data with high noise and high background. Abbassi et al., 141 Mass Spectrum. Ion Proc. 171-86 (1995). One disadvantage of the Abbassi et al. technique is that transformation of the original data is required in order to enhance the quality of the signal.

Other automated methods that are commonly used to distinguish noise and background contributions in complex chromatographic data, and that do not require transformation of the original data include COMPONENT DETECTION ALGORITHM (CODA), U.S. Pat. No. 5,672,869, (Advanced Chemistry Development, Inc., Toronto ON, Canada); TARGETDB (Thru-Put Systems, Inc., Orlando, Fla.); XCALIBUR (Thermo Electron Corporation, San Jose, Calif.); DATAEXPLORER (Applied Biosystems, Foster City, Calif.); and TURBOQUAN (Perkin Elmer Biosystems, Wellesley, Mass.). Each of the non-transforming methods is effective with a targeted approach, but each method breaks down when a non-targeted comprehensive list of compounds present in a chromatogram is desired. In a targeted approach, the methods function by identifying mass ions corresponding to a particular targeted compound as those masses occurring within a pre-determined mass cut-off window on either side of the expected mass of the compound. The size of the mass cut-off window is a function of the resolution of the MS instrument. In the absence of prior knowledge of expected masses (a non-targeted approach), the methods function by assigning mass ions to predetermined groups of an equal size resolution window at evenly spaced intervals. As a result, mass ions that correspond to one particular compound whose chromatographic resolution spans multiple time scans may be incorrectly identified as separate compounds or, vice versa, ions corresponding to separate compounds within a particular time region may be assigned to a single component.

The weaknesses of the non-transforming methods described above when used for non-targeted analysis are not limited to the introduction of errors as describe above, but also include substantial loss of information from data having a high degree of noise and/or a low signal to noise ratio (both of which are typical of metabolic profiling data). For example, the CODA method computes a smoothed and meansubtracted version of each mass chromatogram, compares it with the original chromatogram, and calculates a similarity index between the two. Chromatograms having similarity indices exceeding a threshold value are retained and combined to form a reduced total ion chromatogram, while other chromatograms are rejected. CODA has proven very effective at selecting high-quality mass chromatograms. However, the algorithm is limited to accepting or rejecting entire chromatograms based on noise level, and cannot filter noise from an individual chromatogram. As a result, noisy chromatograms that contain useful information are eliminated, and important peaks may not be detected.

Accordingly, there is a need for improved methods of processing complex chromatographic data in a global or non-targeted manner. The present invention provides such improved methods, which are efficient and minimize loss of information and introduction of error.

SUMMARY OF THE INVENTION

The present invention provides improved methods for non-targeted processing of hyphenated chromatographic data, such that even when the data represent a complex mixture of unknown components, a comprehensive number of the components are detected with minimal loss of information and introduction of error. Processing of hyphenated chromatographic data according to the methods of the invention is compatible with the use of subsequent algorithms for chromatographic information extraction, and enhances the accuracy of a subsequent peak/component picking program. The present invention provides methods for processing hyphenated chromatographic data, the methods comprising, obtaining hyphenated chromatographic data points that each comprise at least three dimensions, one of the dimensions being a continuous dimension; and subjecting at least a portion of the data points to an algorithm that organizes the data points into discrete clusters of the continuous dimension values by starting at either the smallest or largest value and delineating at the largest gap between adjacent values within a predetermined resolution window, resulting in consecutive clusters of varying width of less than or equal to the width of the resolution window.

The methods of the invention comprise subjecting data collected using a hyphenated chromatographic technique such as GC-MS or LC-MS and, thus, data having a continuous or non-discrete dimension (e.g., mass), to an algorithm that organizes the data into discrete groups of the continuous dimension. Determination of the groups of the continuous dimension is by delineation at the largest gap between adjacent continuous dimensions within a predetermined resolution window. Grouping in this manner results in consecutive clusters of continuous dimensions, the clusters having varying width less than or equal to the width of the resolution window. The methods of the invention result in a decreased rate of error relative to the traditional approach, in which data are assigned to predetermined groups of an equal size resolution window at evenly spaced intervals.

In addition to minimizing introduction of error, loss of information is also minimized in the methods of the present invention. Unlike traditional methods in which low quality or noisy data are necessarily discarded, the present methods allow for the retention of information about minor components in noisy chromatograms. Furthermore, the methods of the invention allow for efficient processing of instrument data in profile mode, rather than being limited to the use of centroid data, as is generally the case for traditional methods. For example, the methods of the present invention are particularly useful for chromatography in conjunction with mass spectrometry (MS), in which data are typically not reported as continuous smooth peaks but rather as centroid data (i.e. reduced data where multiple mass peaks have been averaged by the instrument and are reported as a single mass peak). Processing MS data collected in profile mode according to the methods of the invention alleviates the loss of information associated with the centroid process. Even with the substantially larger volume of data present with the use of profile versus centriod collection mode, the current invention provides a processing method that is sufficiently efficient to be completed within the instrument time required for data collection.

Accordingly, use of the methods of the present invention provides numerous advantages, including: efficient data processing; information preservation; resolution, e.g. resolution of isomers with the same mass; and conservation, i.e. original chromatographic data are not transformed.

DETAILED DESCRIPTION OF THE INVENTION

Figure 1:
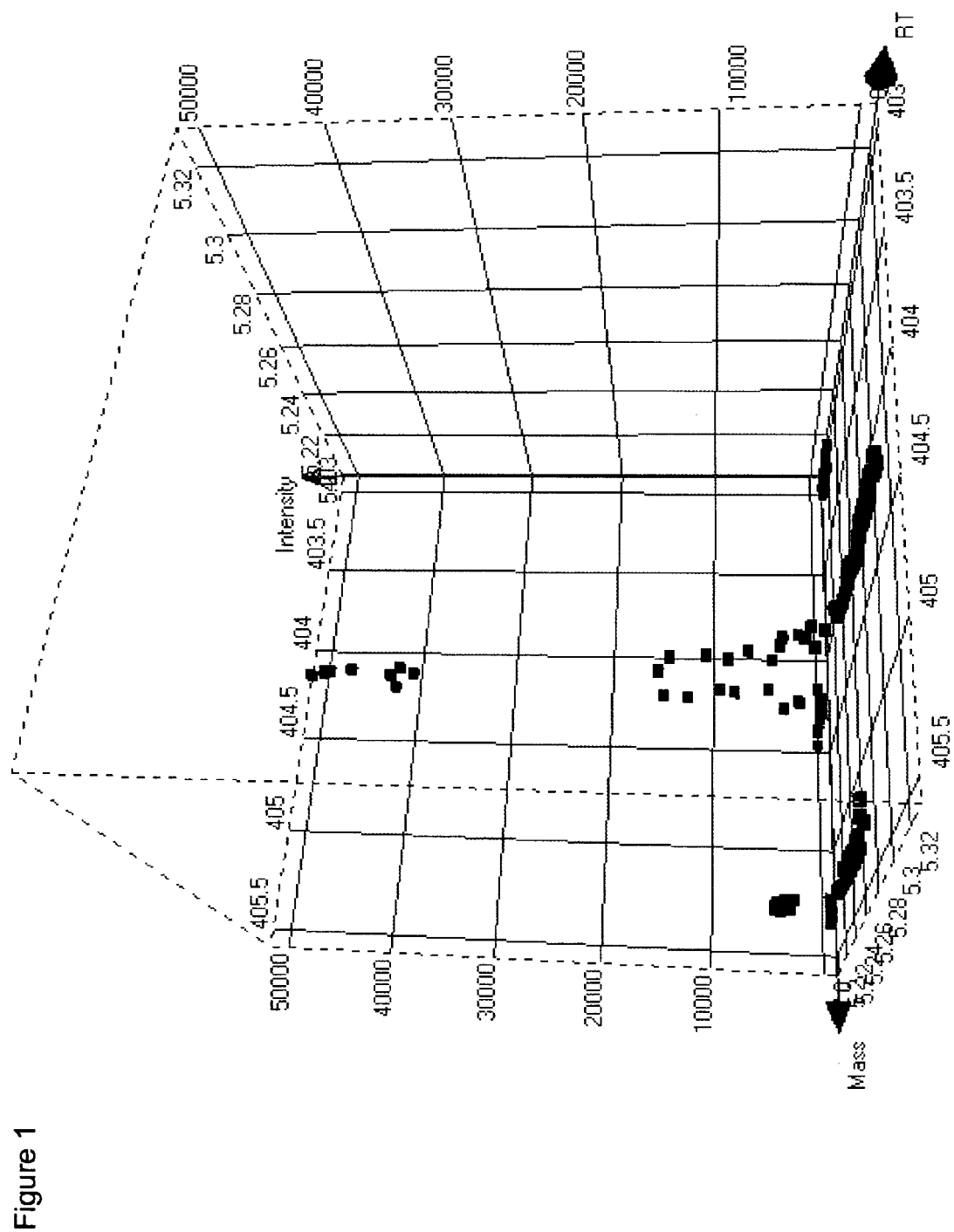
FIG. 1. A three-dimensional plot of raw GC-MS data points having a mass range of about 403-406 amu and a retention time between 5.0 and 5.4 min created using the software program SPOTFIRE (Spotfire, Inc., Somerville, Mass.). The GC-MS data was collected for an *Arabidopsis thaliana* tissue sample using a ThermoFinnigan Tempus gas chromatograph (Thermo Electron Corporation, San Jose, Calif.) coupled with a time of flight mass spectrometer (GC-TOF). The mass resolution for the mass spectrometer employed in this experiment was 1amu.

The present invention provides improved methods for non-targeted or global processing of chromatographic data, such that even when the data represent a complex mixture of unknown components, a comprehensive number of the components are detected efficiently with minimal loss of information and introduction of error. Use of the data processing methods of the present invention is compatible with use of one or more subsequent algorithms for chromatographic information extraction, and results in an enhancement of the accuracy of a subsequent peak/component-picking program.

The methods of the invention are useful for processing data collected using any type of hyphenated chromatographic technique that results in data comprising a continuous or non-discrete dimension. Using the methods of the invention, data collected by a hyphenated chromatographic technique, "hyphenated chromatographic data," are processed such that the continuous aspect of the data is organized into a series of discrete clusters that are representative of the components of the mixture. By "hyphenated chromatographic technique" is meant any chromatography step, including an electrophoresis technique, which is designed to separate mixtures of components followed by one or more spectroscopic or spectrometric detection steps. Types of hyphenated chromatographic data for which the invention is useful are collected by methods that include, for example, gas chromatography- and liquid chromatography-mass spectrometry (GC-MS; LC-MS), liquid chromatography-nuclear magnetic resonance (LC-NMR), liquid chromatography-ultra violet spectroscopy (LC-UV), liquid chromatography-infra red spectroscopy (LC-IR), and liquid chromatography-raman spectroscopy.

The methods of the present invention comprise the steps of obtaining, for a mixture of components, hyphenated chromatographic data points that each comprise at least three dimensions, one of the dimensions being a continuous or non-discrete dimension, and subjecting at least a portion of the data points to an algorithm that organizes the data into discrete clusters of the continuous dimension. Thus, the methods of the invention result in reduction of the continuous aspect of the data into a series of discrete clusters that are representative of the components of the mixture. In such manner, a comprehensive number of the components are detected efficiently with minimal loss of information and introduction of error, and the accuracy of a subsequent peak/component-picking program is enhanced.

Data collected using any one of such hyphenated chromatographic techniques comprises at least three dimensions, one of the dimensions being a continuous or non-discrete dimension. For example, in GC-MS and LC-MS the continuous dimension is mass; in LC-NMR the continuous dimension is magnetic resonance frequency; in LC-UV the continuous dimension is UV absorbance wavelength, etc. The remaining two data dimensions in the hyphenated chromatographic techniques are, for example, sampling time and response. In the particular case of GC-MS or LC-MS, data points are collected each comprising a mass dimension, a scan time (retention time) dimension and a response dimension, the mass dimension being the continuous dimension, and the data points are subjected to an algorithm that organizes the data into discrete groups of the mass dimension. Thus, the method results in reduction of the continuous (mass) aspect of the data into a series of discrete clusters that represent the components of the mixture.

Accordingly, the present invention provides methods for processing hyphenated chromatographic data, the methods comprising, obtaining hyphenated chromatographic data points that each comprise a continuous dimension; and subjecting at least a portion of the data points to an algorithm that organizes the data points into discrete clusters of the continuous dimension values by starting at either the smallest or largest value and delineating at the largest gap between adjacent values within a predetermined resolution window, resulting in consecutive clusters of varying width of less than or equal to the width of the resolution window.

Four preferred embodiments of the present invention are described in further detail herein below, each embodiment exemplified by a particular algorithm. Implementation of any one of the four algorithms provided is not necessarily limited to the exact order of the steps as they appear, as long as the implementation procedure enables proper functioning of the algorithm to achieve the prescribed results. The present invention encompasses implementation procedures known to those of ordinary skill in the art, and such implementation procedures, including but not limited to performing of steps in parallel, may increase or decrease algorithm run-time.

In the first preferred embodiment of the invention, methods are provided for processing hyphenated chromatographic data, the methods comprising obtaining hyphenated chromatographic data points that each comprise at least three dimensions, one of the dimensions is a continuous dimension; and subjecting at least a portion of the data points to an algorithm that organizes the data points into discrete clusters of the continuous dimension values by starting at either the smallest or largest value and delineating at the largest gap between adjacent values within a predetermined resolution window, resulting in consecutive clusters of varying width of less than or equal to the width of the resolution window.

In a particular case that exemplifies the first preferred embodiment, data collected using a hyphenated chromatographic technique, resulting in data comprising a continuous dimension, are processed using an algorithm that functions as follows:

1. Data points are ordered by value of the continuous dimension.
2. Starting at either the smallest or the largest value of the continuous dimension (start value), an end value is found having a distance from the start value that is the minimum that is greater than a designated resolution limit.
3. The data points comprising the start value, the end value, and every value lying between are designated as a subset.
4. The largest gap between any two consecutive values within the subset is located, and the consecutive values are designated as a stop value and a new start value, the stop value being the closer of the two to the original start value.
5. The data points having the values ranging from the original start value up to and including the stop value are marked as a cluster.
6. Steps (2-5) are repeated starting at the new start value, until the number of the data points in the original list is zero.

According to the above-described algorithm, data points collected using a hyphenated chromatographic technique and having a continuous dimension are ordered according to value of the continuous dimension (e.g. in the case of mass spectrometry, data are ordered according to mass value). The data are organized or grouped into clusters of similar masses by delineation at the largest gap between adjacent masses within a predetermined resolution window. The predetermined resolution window is a function of a particular mass spectrometer instrument.

Largest gaps between data points within the resolution window are determined sequentially, starting at either the smallest or the largest of the masses. The data points with masses ranging in value from the starting mass up to and including the first mass defining the largest gap are marked as a cluster. The process is repeated, beginning at the point where the previous cluster ended, such that the data points previously marked as a cluster are effectively excluded from the remaining list of data points to be processed, until all of the data points have been marked as a cluster. The methods of the invention result in data points being grouped into consecutive clusters of varying width that is less than or equal to the width of the resolution window, in contrast to traditional non-targeted processing methods in which data points are assigned to predetermined groups of an equal size resolution window at evenly spaced intervals. Allowing the cluster width to vary in such a manner according to the data, rather than enforcing a predetermined window, minimizes the chances of single components being incorrectly split up or multiple components being incorrectly combined.

Processing of hyphenated chromatographic data according to the methods of the invention is compatible with the use of one or more subsequent algorithms for information extraction, and facilitates the accuracy of a subsequent peak/component-picking program. For example, in one embodiment of the invention, data that have been processed according to the methods of the invention are further processed prior to peak picking through inclusion to the algorithm of an additional step. The additional step comprises replacing the range of continuous dimension values for each cluster with a single representative continuous dimension value. One example of use of a single representative value is replacement of the range of values in a cluster with a weighted average value for the cluster that has an instrument response equal to the sum for all the data points. Conversion of the data in each of the clusters to weighted average values is only one example of a multitude of methods by which the data may be represented or further manipulated, and is not intended to be limiting.

In addition to minimizing introduction of error, loss of information is also minimized through use of the methods of the present invention. Unlike certain traditional methods in which low quality or noisy data are necessarily discarded, the present methods allow for the retention of information about minor components in noisy chromatograms. Another advantage of the invention is that the methods allow for efficient processing of instrument data in profile or in centroid mode rather than being limited to the use of centroid data, as is typically the case for traditional methods. For example, the methods of the present invention are particularly useful for chromatography in conjunction with mass spectrometry (MS), in which data are typically not reported as continuous smooth peaks but rather as centroid data (i.e. reduced data where multiple mass peaks are averaged at the instrument and reported as a single mass peak). Processing MS data collected in profile mode according to the methods of the invention alleviates the loss of information associated with use of centroid data.

The second preferred embodiment of the present invention provides a modification of the first preferred embodiment that is particularly well suited for processing hyphenated chromatographic data that has a high degree of noise. In the second preferred embodiment, methods are provided for processing hyphenated chromatographic data, the methods comprising obtaining hyphenated chromatographic data points that each comprise at least three dimensions, wherein one of the dimensions is a response dimension and one of the dimensions is a continuous dimension; and subjecting at least a portion of the data points to an algorithm that partitions the data points into a high response dimension group and a low response dimension group according to a designated threshold; and organizes the data points of the high response dimension group into discrete clusters of the continuous dimension values by starting at either the smallest or largest value and delineating at the largest gap between adjacent values within a predetermined resolution window, resulting in consecutive clusters of varying width of less than or equal to the width of the resolution window.

In a particular case that exemplifies the second preferred embodiment, data collected using a hyphenated chromatographic technique, resulting in data comprising a continuous dimension, are processed using an algorithm that functions as follows:

1. Data points are partitioned into a high instrument response group and a low instrument response group according to a designated threshold.
2. The high response group of data points is ordered by value of the continuous dimension.
3. For the high response group, starting at either the smallest or the largest value of the continuous dimension, an end value is found having a distance from the start value that is the minimum that is greater than a designated resolution limit.
4. The data points comprising the start value, the end value, and every value lying between are designated as a subset.
5. The largest gap between any two consecutive values within the subset is located, and the consecutive values are designated as a stop value and a new start value, the stop value being the closer of the two to the original start value.
6. The data points having the values ranging from the original start value up to and including the stop value are marked as a cluster.
7. Steps (3-6) are repeated beginning at the new start value, until the number of the data points in the high response group is zero.

The foregoing embodiment differs from the first preferred embodiment in the inclusion of a step in which the data points are partitioned into a high and a low instrument response group. There is no difference in the remaining steps of the two methods, except that the remaining steps in the foregoing method are performed with only the high intensity group of data points. Addition of the partitioning step in the second embodiment allows for exclusion of data points with an instrument response time that is lower than a user defined threshold. In this manner, the influence of noisy data on the clustering algorithm is minimized, and the determination of an acceptable instrument response is in the control of the user.

The invention also provides related methods of the foregoing embodiment in which the data are split into a high and low response group that further involve addition of all or a portion of the low instrument response data to the data clusters. For example, in one embodiment of the invention, subsequent to cluster formation, all or a portion of the low instrument response data are assigned according to continuous dimension value to the cluster to which they fall within range. In a similar embodiment, subsequent to cluster formation, the continuous dimension value range of each of the clusters is expanded at both the lowest value and the highest value by a factor epsilon. The low response data are assigned according to continuous dimension value to the expanded range cluster to which they fall within range. Each of the data points in the low response group is assigned to no more than one of the clusters. By including all or a portion of the low response data in the clusters, the low responses are not completely excluded from analysis, but these data do not contribute to the formation of the cluster groups.

Similar to that described for the first preferred embodiment, processing of hyphenated chromatographic data according to the second preferred embodiment is compatible with the use of one or more subsequent algorithms for information extraction. For example, in related embodiments of the invention, data that have been processed according to any of the foregoing methods are further processed prior to peak picking through inclusion to the algorithm of an additional step. The additional step comprises replacing the range of continuous dimension values for each cluster with a single representative continuous dimension value. One example of a single representative value is a weighted average value having an instrument response equal to the sum for all the data points. Again, conversion of the data in each of the clusters to weighted average values is only one example of a multitude of methods by which the data may be represented or further manipulated, and is not intended to be limiting.

The third preferred embodiment of the present invention provides methods that are particularly useful for processing hyphenated chromatographic data collected in profile mode. Use of profile versus centroid mode data is advantageous, as information is lost in the centroid process. In the methods, data collected using a hyphenated chromatographic technique that results in data comprising at least three dimensions, one of the dimensions is a continuous dimension and one of the dimensions is a discrete dimension, the data are processed by first clustering the continuous dimension values within each discrete dimension value, and next clustering the resulting data across the entire range of discrete dimension values. One particular example is use of hyphenated chromatographic/mass spectrometric data having a mass continuous dimension and a scan time discrete dimension.

The third preferred embodiment provides methods for processing hyphenated chromatographic data, the methods comprising,
- a) obtaining hyphenated chromatographic data points that each comprise at least three dimensions, one of the dimensions is a continuous dimension and one of the dimensions is a discrete dimension; and
- b) subjecting at least a portion of the data points to an algorithm that:
  - i) organizes the data points, within each discrete dimension value, into clusters of the continuous dimension values by starting at either the smallest or largest value and delineating at the largest gap between adjacent values within a predetermined resolution window, resulting in consecutive clusters of varying width of less than or equal to the width of the resolution window;
  - ii) calculates a single representative continuous dimension value for each cluster; and
  - iii) repeats step (i) over the entire range of the discrete dimension values using the single representative continuous dimension values, resulting in consecutive clusters of representative values of varying width of less than or equal to the width of the resolution window.

In a particular case exemplifying the third embodiment, data comprising at least three dimensions, one of the dimensions a continuous dimension and one of the dimensions a discrete dimension, are processed using an algorithm that functions as follows:
1. Data points having a first discrete dimension are ordered by value of the continuous dimension.
2. Starting at either the smallest or the largest value, an end value is found having a distance from the start value that is the minimum that is greater than a designated resolution limit.
3. The data points comprising the start value, the end value, and every value lying between are designated as a subset.
4. The largest gap between any consecutive two of the values of the subset is located and the consecutive two of the values are designated as a stop value and a new start value, the stop value being the closer of the two to the original start value.
5. The data points having the values ranging from the original start value up to and including the stop value are marked as a cluster.
6. Steps (1-5) are repeated using the new start value, until the number of the data points in step (1) is zero.
7. Steps (1-6) are repeated for each of the remaining discrete dimension values of the original list of data points.
8. A single representative continuous dimension value is calculated for each cluster of step (5), and the calculated single representative continuous dimension values are ordered by value.
9. Steps (2-6) are repeated using the single representative continuous dimension values until the number of representative values is zero, resulting in consecutive clusters of the single representative continuous dimension values that have a varying width of less than or equal to the width of the resolution window.

Like the preceding embodiments described herein, processing of hyphenated chromatographic data according to the third preferred embodiment results in the data being grouped into a series of consecutive clusters of varying width that is less than or equal to the width of the resolution window. The foregoing method differs from the earlier described methods in that data points are first clustered within each discrete dimension, a single representative continuous dimension value is calculated for the clusters, and then the calculated representative data are used to cluster over the entire range of discrete dimension values. One example of a single representative value is a weighted average value, as described herein above. Implementation of the successive clustering according to the methods of the invention provides an efficient mechanism for processing of profile mode data that enables a higher level of accuracy in assignment of data points to clusters than is possible with use of centroid data. Thus, the methods of the invention minimize both introduction of error and loss of information.

As is the case for the earlier described embodiments, processing of hyphenated chromatographic data according to the third preferred embodiment is compatible with the use of one or more subsequent algorithms for information extraction. For example, in related embodiments of the invention, data that have been processed according to the foregoing method are further processed prior to peak picking through inclusion to the algorithm of an additional step. The additional step comprises replacing each cluster of single representative continuous dimension values with a final single representative continuous dimension value. In one embodiment, the final single representative value is a weighted average value having an instrument response equal to the sum for all the data points. However, the weighted average value is only one example of a multitude of methods by which the data may be represented or further manipulated, and is not intended to be limiting.

The fourth preferred embodiment of the invention provides methods that are particularly useful for processing hyphenated chromatographic data collected in profile mode and having a high degree of noise. In the fourth preferred embodiment, data collected using a hyphenated chromatographic technique that results in data comprising at least three dimensions, a continuous dimension, a discrete dimension, and a response dimension, are processed by first partitioning the data into a high and low response group, clustering the continuous dimension values of the high intensity group within each discrete dimension value, and finally clustering the resulting data across the entire range of discrete dimension values. One particular example of the fourth preferred embodiment of the invention is use of hyphenated chromatographic/mass spectrometric data having a mass continuous dimension, a scan time discrete dimension, and an instrument response dimension.

The fourth preferred embodiment provides methods for processing hyphenated chromatographic data, the methods comprising,
- a) obtaining hyphenated chromatographic data points that each comprise a continuous dimension, a discrete dimension, and a response dimension; and
- b) subjecting at least a portion of the data points to an algorithm that:
  - i) partitions the data points into a high response dimension group and a low response dimension group according to a designated threshold;

ii) organizes the high response dimension group of data points, within each discrete dimension value, into discrete clusters of the continuous dimension values by starting at either the smallest or largest value and delineating at the largest gap between adjacent values within a predetermined resolution window, resulting in consecutive clusters of varying width of less than or equal to the width of the resolution window;

iii) calculates a single representative continuous dimension value for each cluster; and iv) repeats step (ii) over the entire range of the discrete dimension values using the calculated single representative continuous dimension values, resulting in consecutive clusters of the representative values that have a varying width of less than or equal to the width of the resolution window.

In a particular case that exemplifies the fourth preferred embodiment, data comprising at least three dimensions, a continuous-, discrete- and response-dimension, are processed using an algorithm that functions as follows:

1. The data points are partitioned into a high response dimension group and a low response dimension group according to a designated threshold.
2. The high response dimension data points having a first discrete dimension are ordered by value of the continuous dimension.
3. Starting at either the smallest or the largest value, an end value is found having a distance from the start value that is the minimum that is greater than a designated resolution limit.
4. The data points comprising the start value, the end value, and every value lying between are designated as a subset.
5. A largest gap is located between two consecutive values of the subset, and the consecutive two values are designated as a stop value and a new start value, the stop value being the closer of the two to the original start value.
6. The data points having the values ranging from the original start value up to and including the stop value are marked as a cluster.
7. Steps (3-6) are repeated using the new start value, until the number of the data points having the first discrete dimension value (step 2) is zero.
8. Steps (2-7) are repeated for each of the discrete dimension values of the remaining high response dimension group of data points in step (1).
9. A single representative continuous dimension value is calculated for each cluster of step (6), and the calculated single representative continuous dimension values are ordered by value.
10. Steps (3-7) are repeated using the single representative continuous dimension values until the number of the representative values is zero, resulting in consecutive clusters of the representative values that have a varying width of less than or equal to the width of the resolution window.

As described for the previous embodiment, implementation of successive clustering according to the foregoing embodiment provides an efficient mechanism for processing of profile mode data that enables a higher level of accuracy in assignment of data points to clusters than is possible with use of centroid data. Thus, the methods of the fourth preferred embodiment of the invention minimize both introduction of error and loss of information. In addition to enabling use of profile mode data, the methods of the fourth preferred embodiment facilitate accurate processing of hyphenated chromatographic data having a high degree of noise. A step is included in the fourth preferred embodiment in which the data points are partitioned into a high and a low instrument response group, such that the clustering algorithm is performed on only the high intensity group of data points. Addition of such a step allows for exclusion of data points with an instrument response time that is lower than a user defined threshold. In this manner, the influence of noisy data on the clustering algorithm is minimized, and the determination of an acceptable instrument response is in the control of the user.

The present invention encompasses related methods of the fourth preferred embodiment that further involve addition of all or a portion of the low instrument response data to the data clusters. For example, in one embodiment, subsequent to cluster formation all or a portion of the low instrument response data are assigned according to continuous dimension value to the cluster to which they fall within range. In a similar embodiment, subsequent to cluster formation, the continuous dimension range of each of the clusters is expanded at both the lowest continuous dimension value and the highest continuous dimension value by a factor epsilon. The low response data are assigned according to continuous dimension value to the expanded range cluster to which they fall within range. Each of the data points in the low response group is assigned to no more than one of the clusters. By including all or a portion of the low response data in the clusters, the low responses are not completely excluded from analysis, but these data do not contribute to the formation of the cluster groups.

Processing of hyphenated chromatographic data according to the foregoing preferred embodiment is compatible with the use of one or more subsequent algorithms for information extraction. For example, in related embodiments of the invention, data that have been processed according to any of the foregoing methods are further processed prior to a peak/component-picking program through inclusion to the foregoing method of an additional step. The additional step comprises replacing the clusters consisting of single representative continuous dimension values with a final single representative continuous dimension value. In one related embodiment, the final single representative value is a weighted average value having an instrument response equal to the sum for all the data points. However, the weighted average value is only one example of a multitude of methods by which the data may be represented or further manipulated, and is not intended to be limiting.

EXPERIMENTAL

Example 1

The following illustrates processing of GC-MS data according to the methods of the invention.

Sample Preparation

*Arabidopsis thaliana* leaf tissue was derivatized for GC-MS analysis as follows. Plant tissue samples were lyophilized to complete dryness (24-72 hours) and the lyophilized samples were placed into the wells of a 96-well plate. 100 µL of 25% methyl trimethylsilyl trifluoroacetamide (MSTFA) in acetonitrile w/0.1% trifluoroacetic acid (TFA) was added to each well and the plate was heat sealed to protect from moisture. The plate was placed on a shaker for ~5 min and incubated at 60° C. for 15 min without allowing to reach dryness. 100 µL of 25:25:50 acetonitrile: dimethoxyethane: trimethylsilyl dimethylamine (ACN:DME:TMS-DMA) was added to each of the wells and allowed to shake for ~1 min. The plate was incubated at 60° C. for 30 min. The sealing film was removed from the plate and 250 µL of dioxane added to each well. The plate was placed on a shaker for ~1 min. The plate was heat sealed and centrifuged at ~4000 rpm for 5 min. The samples were analyzed by GC-MS.

GC-MS Analysis

GC-MS analysis of the derivatized plant tissue samples was performed on a ThermoFinnigan Tempus gas chromatograph coupled with a time of flight mass spectrometer (GC-TOF) (Thermo Electron Corporation, San Jose, Calif.). The mass resolution for the mass spectrometer employed in this experiment was 1 amu. Compounds detected by GC-MS with an electron impact (EI) ion source were cataloged based on Kovats retention indices and mass-to-charge ratio (m/z) of the ions characteristic of each peak. Mass spectrometric data were collected from 50-800 amu.

Data Processing

The raw mass spectrometric data, collected in profile mode, was converted to a standardized format and processed according to the methods of the invention described herein in which the ten-step algorithm is used for processing of hyphenated chromatographic data collected in profile mode and having a high degree of noise. The computer used for the data conversion and processing was a Dell PowerEdge 6400 Windows 2000 server with a 750 MHz Intel Pentium 3 Xeon microchip and 2 GB RAM, resulting in a 320 sec completion time. In addition, the original raw data was processed using the commercially available software TARGETDB (Thru-Put Systems, Inc., Orlando, Fla.) to demonstrate the differences in results produced using the methods of the invention versus a traditional approach.

Figure 2:
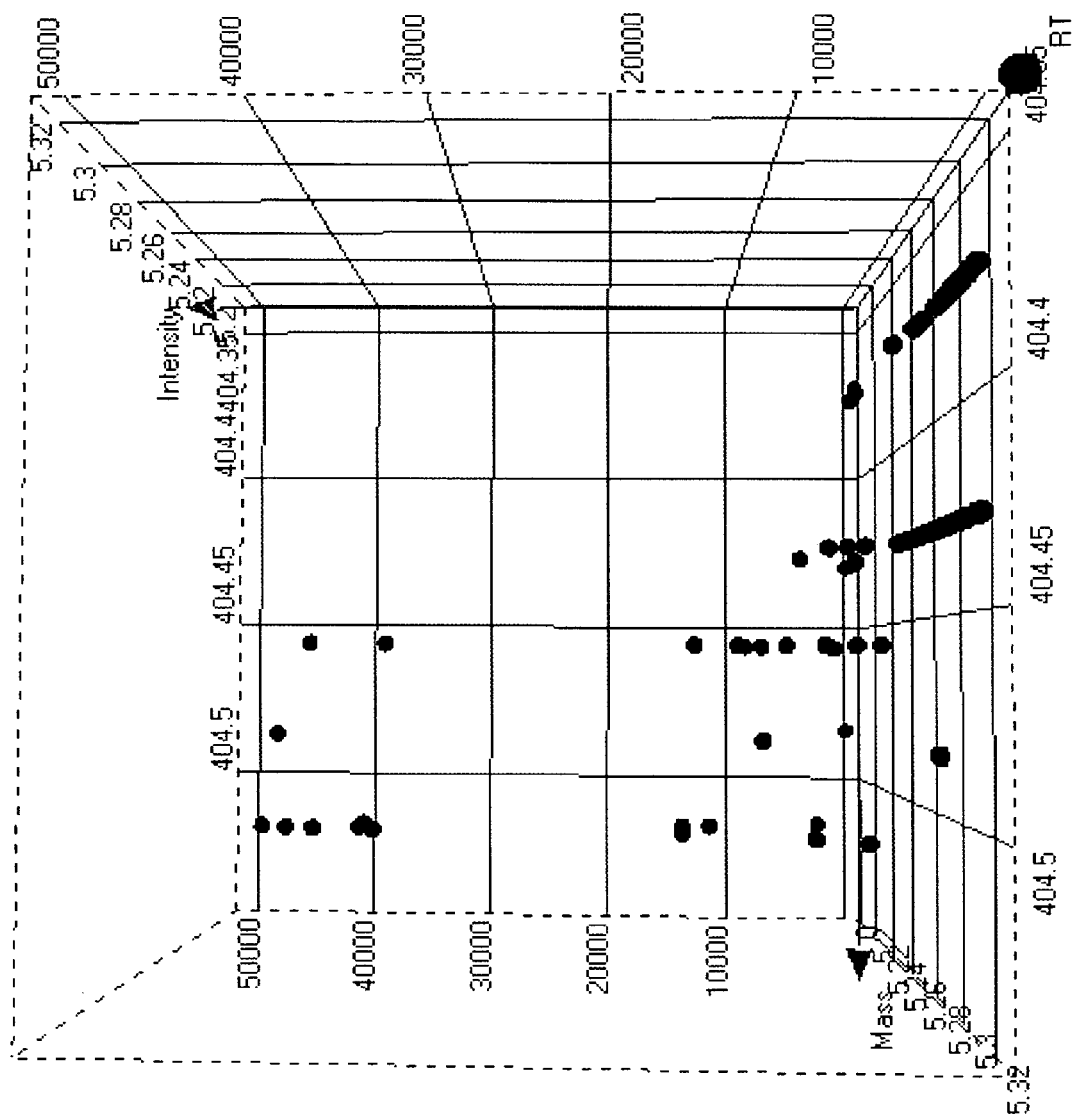
FIG. 2. An expanded view of a portion of the three-dimensional plot of FIG. 1 covering mass range 404.35-404.55 amu.

FIG. 1 depicts a three dimensional plot of the raw data points with a mass between about 403 and 406 amu and a retention time between 5.0 and 5.4 min using the software program SPOTFIRE (Spotfire, Inc., Somerville, Mass.). The masses displayed in FIG. 1 fall into three reasonably distinct groups at estimated values of 403, 404.5, and 405.5 amu. Focusing on the 404.5 amu component illustrates the different results obtained when the data are processed in a non-targeted manner using a traditional approach, versus using the methods of the current invention. FIG. 2 offers an expanded view of mass range 404.35-404.55 amu, and a closer look at the collection of data points near 404.5 amu reveals a number of data points with a mass above 404.5 amu. To demonstrate the advantages of the clustering methods of the invention over traditional methods, the data displayed in FIG. 1 was processed using both TARGETDB software and the methods of the invention.

Figure 3:
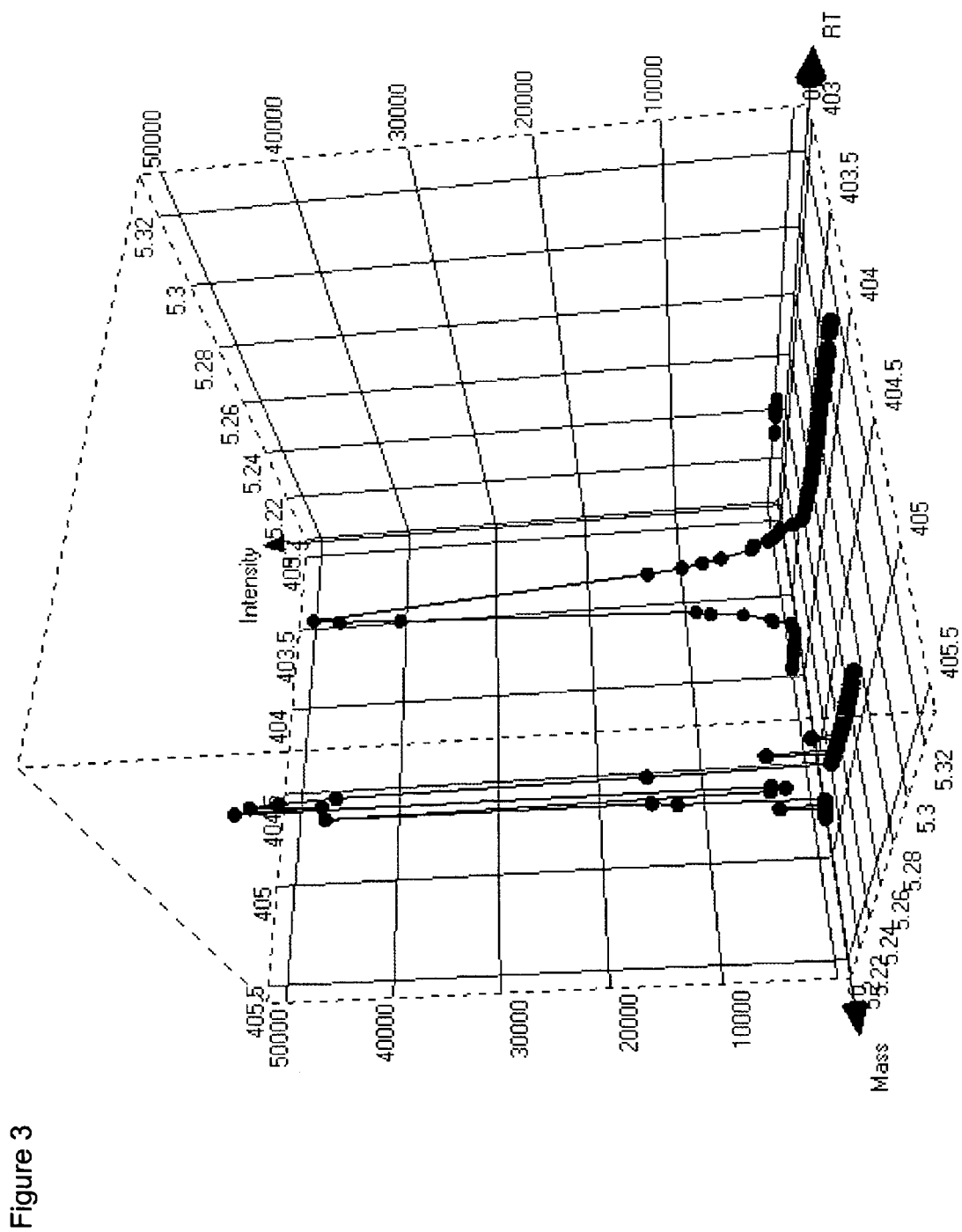
FIG. 3. A three-dimensional plot of the data displayed in FIG. 1, subsequent to processing using TARGETDB software (Thru-Put Systems, Inc., Orlando, Fla.).

For analysis using TARGETDB, a mass of 404 amu was entered into the program to represent the expected component at 404.5 amu. As the data were collected on an instrument with a mass resolution of 1 amu, the program assigned each of the data points having a mass between 403.5 and 404.5 amu and having the same scan time as the 404.5 amu component together as mass 404 amu (FIG. 3). Data points with mass greater than 404.5 amu were assigned together as mass 405 amu. The problem is that the data points with mass greater than 404.5 amu should have been assigned with the data points between 404.45 and 404.5 amu, a point made clear by comparing the raw data of FIG. 1 with the data processed using TARGETDB in FIG. 3. The inconsistencies between the raw and TARGETDB processed data indicate that the single peak at 404.5 amu was incorrectly split in two.

Figure 4:
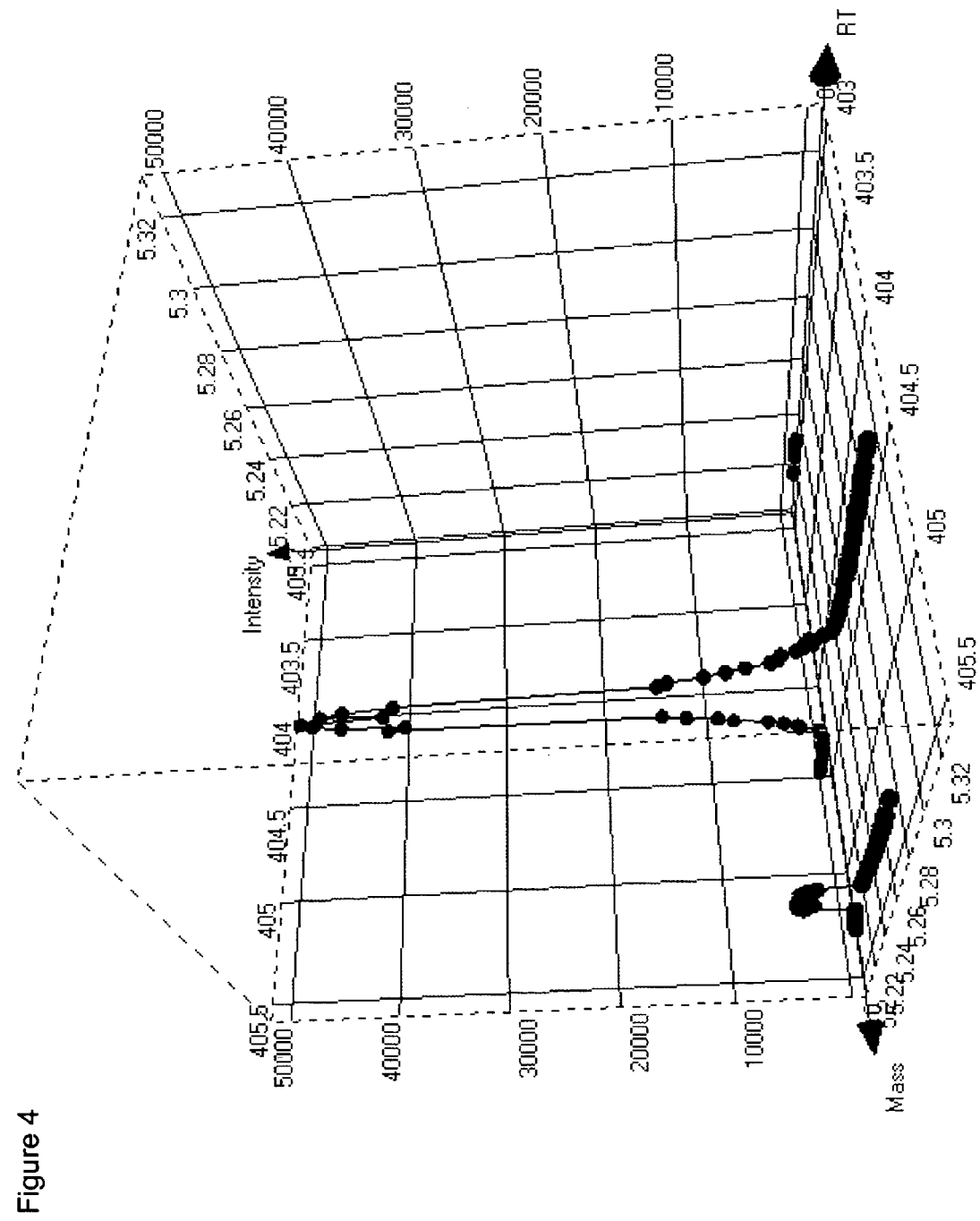
FIG. 4. A three-dimensional plot of the data displayed in FIG. 1, subsequent to processing using the methods of the invention.

In contrast, when the data were processed according to the methods of the invention, the data points with mass values just above 404.5 amu were correctly grouped with the data points having mass values just below 404.5 amu (FIG. 4). The correctness of the grouping is evidenced by the high degree of similarity between the grouping of the data points in the raw data and that of the data points clustered according to the methods of the invention (compare FIGS. 1 and 4). Furthermore, a peak-picking algorithm was applied to the data processed according to the methods of the invention, and the ratio of the integrated areas of the peaks at 405.5 and 404.5 amu is consistent with the peak at 405.5 amu being due to a naturally occurring carbon isotope ($^{13}C$) of the component 404.5 amu.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

While the forgoing describes certain embodiments of the invention, it will be understood by those skilled in the art that variations and modifications may be made and still fall within the scope of the invention.

What is claimed is:

1. A method for processing hyphenated chromatographic data to delineate components of a sample, the method comprising:
   a) obtaining hyphenated chromatographic data points for a sample that each comprise at least three dimensions, at least one of the dimensions being a continuous dimension;
   b) subjecting at least a portion of the data points to an algorithm that organizes the data points into discrete clusters according to the data points' continuous dimension values by starting at either a smallest or largest continuous dimension value associated with data points that are not yet associated with a discrete cluster and delineating, at the largest gap between continuous dimension values of adjacent data points within a predetermined resolution window, a boundary between discrete clusters, wherein the clusters of data points are of varying width of less than or equal to the width of the resolution window and wherein at least some of the clusters of data points are indicative of components of the sample, wherein step b) is repeated until all data points are associated with a cluster; and
   c) outputting to a user information describing the clusters in a user-readable format, wherein the steps a), b), and c) are performed on a suitably-configured computer and wherein the algorithm functions according to the following steps:
      i. creating an ordered set of the continuous dimension values of the data points;
      ii. selecting, as a start value, either the smallest or the largest value within the ordered set;
      iii. finding, as an end value, a value within the ordered set that is the closest to the start value from among the values having a distance from the start value that is greater than a designated resolution limit;
      iv. designating as a subset the values of the ordered set comprising the start value, the end value, and every value lying between;
      v. locating a largest gap between any consecutive two of the values of the subset, and designating the consecutive values as a stop value and a restart value, the stop value being the closer of the two to the start value;
      vi. marking as a cluster the data points having a continuous dimension value ranging from the start value up to and including the stop value; and
      vii. repeating steps (iii-vi) using the restart value as the start value, until each data point is contained within a marked cluster.

2. The method of claim 1 wherein the three dimensions consist of a continuous dimension, a discrete dimension and a response dimension.

3. The method of claim 2 wherein the continuous dimension is a mass dimension, the discrete dimension is a scan time dimension, and the data points are collected using a mass spectrometer.

4. The method of claim 3 wherein the data points are collected in centroid mode.

5. The method of claim 3 wherein the data points are collected in profile mode.

6. The method of claim 1 wherein the algorithm calculates for each cluster a single representative continuous dimension value.

7. The method of claim 6 wherein the single representative continuous dimension value is a weighted average value.

8. A method for processing hyphenated chromatographic data to delineate components of a sample, the method comprising:
   a) obtaining hyphenated chromatographic data points for a sample that each comprise at least three dimensions, one of the dimensions being a response dimension and one of the dimensions being a continuous dimension;
   b) subjecting at least a portion of the data points to an algorithm that:
      i) partitions the data points into a high response dimension group and a low response dimension group according to a designated response dimension value threshold;
      ii) organizes the data points of the high response dimension group into discrete clusters according to the high response dimension group data points' continuous dimension values by starting at either the smallest or largest continuous dimension value associated with data points that are not yet associated with a discrete cluster and delineating, at the largest gap between continuous dimension values of adjacent data points within a predetermined resolution window, a boundary between discrete clusters, wherein the clusters of high response dimension group data points are of varying width of less than or equal to the width of the resolution window and wherein at least some of the clusters of high response dimension group data points are indicative of components of the sample, wherein step b) is repeated until all data points of the high response dimension group are associated with a cluster; and
   c) outputting to a user information describing the clusters in a user-readable format, wherein the steps a), b), and c) are performed on a suitably-configured computer and wherein the algorithm functions according to the following steps:
      i. creating an ordered set of the continuous dimension values of the data points within the high response dimension group;
      ii. selecting, as a start value, either the smallest or the largest value within the ordered set;
      iii. finding, as an end value, a value within the ordered set that is the closest to the start value from among the values having a distance from the start value that is greater than a designated resolution limit;
      iv. designating as a subset the values of the ordered set comprising the start value, the end value, and every value lying between;
      v. locating a largest gap between any consecutive two of the values of the subset, and designating the two consecutive values as a stop value and restart value, the stop value being the closer of the two to the start value;
      vi. marking as a cluster the high response dimension group data points having a continuous dimension value ranging from the start value up to and including the stop value; and
      vii. repeating steps (iii-vi) using the restart value as the start value, until each data point is contained within a marked cluster.

9. The method of claim 8 wherein the third dimension is a discrete dimension.

10. The method of claim 9 wherein the continuous dimension is a mass dimension, the discrete dimension is a retention time dimension, and the data points are collected using a mass spectrometer.

11. The method of claim 10 wherein the data points are collected in centroid mode.

12. The method of claim 10 wherein the data points are collected in profile mode.

13. The method of claim 8 wherein for each cluster of high response dimension group data points, the data points in the low response dimension group having continuous dimension values that fall within the continuous dimension value range of the cluster are added to the cluster.

14. The method of claim 8 wherein the continuous dimension value range of each of the clusters is expanded at both the lowest continuous dimension value and the highest continuous dimension value by a factor epsilon, and the algorithm adds to each expanded cluster the data points in the low response dimension group having continuous dimension values that fall within the expanded range of the cluster, each of the data points in the low response dimension group being added to only one of the expanded clusters.

15. The method of claim 8 wherein the algorithm calculates for each cluster a single representative continuous dimension value.

16. The method of claim 15 wherein the single representative continuous dimension value is a weighted average value.

17. A method for processing hyphenated chromatographic data to delineate components of a sample, the method comprising:
   a) obtaining hyphenated chromatographic data points for a sample that each comprise at least three dimensions, one of the dimensions being a continuous dimension and one of the dimensions being a discrete dimension;
   b) subjecting at least a portion of the data points to an algorithm that:
      i) organizes the data points within each discrete dimension value into clusters according to the data points' continuous dimension values by starting at either the smallest or largest continuous dimension value associated with data points that are not yet associated with a discrete cluster and delineating, at a largest gap between continuous dimension values of adjacent data points within a predetermined resolution window, a boundary between discrete clusters, wherein the clusters of data points are of varying width of less than or equal to the width of the resolution window, wherein step i) is repeated until all data points are associated with a cluster;
      ii) for each cluster of data points, calculates a single representative continuous dimension value for the cluster and associates the calculated representative continuous dimension value to each data point in the cluster; and iii) organizes the data points, regardless of discrete dimension value, into groups according to their representative continuous dimension values, wherein the groups are of varying width of less than or equal to the width of the resolution window and wherein at least some of the groups are indicative of components of the sample; and c) outputting to a user information describing the groups in a user-readable format, wherein the steps a), b), and c) are performed on a suitably-configured computer and wherein the algorithm functions according to the following steps:

i. creating an ordered set of the continuous dimension values of data points having a first discrete dimension value;

ii. selecting, as a start value, either the smallest or the largest value within the ordered set and finds, as an end value, a value within the ordered set that is the closest to the start value from among the values having a distance from the start value that is greater than a designated resolution limit;

iii. designating as a subset the values of the ordered set comprising the start value, the end value, and every value lying between;

iv. locating a largest gap between any consecutive two of the values of the subset, and designating the two consecutive values as a stop value and a restart value, the stop value being the closer of the two to the start value;

v. marking as a cluster the data points having a continuous dimension value ranging from the start value up to and including the stop value;

vi. repeating steps (ii-v) using the restart value as the start value, until each data point having the first discrete dimension value is contained within a marked cluster;

vii. repeating steps (i-vi) for each of the discrete dimension values of the remaining original data points;

viii. calculating for each cluster of data points of step (v) a single representative continuous dimension value, associating the calculated representative continuous dimension value to each data point in the cluster, and ordering by value the calculated single representative continuous dimension values; and ix. repeating steps (ii-vi) using the single representative continuous dimension values until the number of the remaining representative values is zero, resulting in data points organized into groups according to consecutive clusters of the representative values, the clusters having varying width of less than or equal to the width of the resolution window.

18. The method of claim 17 wherein the third of the dimensions is a response dimension.

19. The method of claim 18 wherein the continuous dimension is a mass dimension, the discrete dimension is a scan time dimension, and the data points are collected using a mass spectrometer.

20. The method of claim 19 wherein the data points are collected in profile mode.

21. The method of claim 17 wherein the algorithm calculates for each cluster of representative values a final single representative continuous dimension value.

22. The method of claim 21 wherein the final single representative continuous dimension value is a weighted average value.

23. A method for processing hyphenated chromatographic data to delineate components of a sample, the method comprising:

a) obtaining hyphenated chromatographic data points for a sample that each comprise a continuous dimension, a discrete dimension, and a response dimension;

b) subjecting at least a portion of the data points to an algorithm that:

i) partitions the data points into a high response dimension group and a low response dimension group according to a designated response dimension value threshold;

ii) organizes the high response dimension group of data points having a first discrete dimension value into discrete clusters according to the high response dimension group data points' continuous dimension values by starting at either the smallest or largest continuous dimension value associated with data points that are not yet associated with a discrete cluster and delineating at the largest gap between continuous dimension values of adjacent data points within a predetermined resolution window, a boundary between discrete clusters, wherein the clusters of high response dimension group data points are of varying width of less than or equal to the width of the resolution window, wherein step i) is repeated until all data points are associated with a cluster;

iii) for each cluster of data points, calculates a single representative continuous dimension value for the cluster and associates the calculated representative continuous dimension value to each data point in the cluster;

iv) repeats steps (ii) and (iii) over the entire range of the discrete dimension values; and v) organizes the data points, regardless of discrete dimension value, into groups according to their representative continuous dimension values wherein the groups are of varying width of less than or equal to the width of the resolution window and wherein at least some of the clusters are indicative of biochemical components of the sample; and c) outputting to a user information describing the groups in a user-readable format, wherein the steps a), b), and c) are performed on a suitably-configured computer and wherein the algorithm functions according to the following steps:

i. partitioning the data points into a high response dimension group and a low response dimension group according to a designated response dimension value threshold;

ii. creating an ordered set of the continuous dimension values of data points in the high response dimension group having a first discrete dimension value;

iii. selecting, as a start value, either the smallest or the largest value within the ordered set and finds, as an end value, a value within the ordered set that is the closest to the start value from among the values having a distance from the start value that is greater than a designated resolution limit;

iv. designating as a subset the values of the ordered set comprising the start value, the end value, and every value lying between;

v. locating a largest gap between any consecutive two of the values of the subset, and designating the consecutive values as a stop value and a restart value, the stop value being the closer of the two to the start value;

vi. marking as a cluster the data points having a continuous dimension value ranging from the start value up to and including the stop value;

vii. repeating steps (iii-vi) using the restart value as the start value, until each data point in the high response dimension group having the first discrete dimension value is contained within a marked cluster;

viii. repeating steps (ii-vii) for each of the discrete dimension values of the data points remaining in the high response dimension group;

ix. calculating for each cluster of data points of step (vi) a single representative continuous dimension value, associating the calculated representative continuous dimension value to each high response dimension group data point in the cluster, and ordering by value the single representative continuous dimension values; and x. repeating steps (iii-vii) using the single representative continuous dimension values until the number of the remaining representative values is zero, resulting in high response dimension group data points organized into groups according to consecutive clusters of the representative values, the clusters having a varying width of less than or equal to the width of the resolution window.

24. The method of claim 23 wherein the continuous dimension is a mass dimension, the discrete dimension is a scan time dimension, and the data points are collected using a mass spectrometer.

25. The method of claim 24 wherein the data points are collected in profile mode.

26. The method of claim 23 wherein for each group, the data points in the low response dimension group having continuous dimension values that fall within the continuous dimension range of the data points within the group are added to the group.

27. The method of claim 23 wherein the continuous dimension range of each of the clusters of the representative values is expanded at both the lowest continuous dimension value and the highest continuous dimension value by a factor epsilon, and the algorithm adds to each expanded cluster the data points in the low response dimension group having continuous dimension values that fall within the expanded range of the cluster, each of the data points in the low response dimension group being added to only one of the expanded clusters.

28. The method of claim 23 wherein the algorithm calculates for each cluster of the representative values a final single representative continuous dimension value.

29. The method of claim 28 wherein the final single representative value is a weighted average value.

30. The method of claim 1 comprising using the clusters of data points to identify the biochemical components of the sample.

31. The method of claim 8 comprising using the clusters of data points to identify the biochemical components of the sample.

32. The method of claim 17 comprising using the clusters of data points to identify the biochemical components of the sample.

33. The method of claim 23 comprising using the clusters of data points to identify the biochemical components of the sample.

* * * * *